(12) United States Patent
Sarkar

(10) Patent No.: US 10,603,309 B2
(45) Date of Patent: *Mar. 31, 2020

(54) ACCELERATING THROMBUS RESOLUTION THROUGH AUGMENTATION OF P53 ACTIVITY

(71) Applicant: Rajabrata Sarkar, Ellicott City, MD (US)

(72) Inventor: Rajabrata Sarkar, Ellicott City, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/918,324

(22) Filed: Mar. 12, 2018

(65) Prior Publication Data

US 2018/0200237 A1    Jul. 19, 2018

Related U.S. Application Data

(63) Continuation of application No. 13/501,278, filed as application No. PCT/US2010/051031 on Oct. 1, 2010, now Pat. No. 9,913,832.

(60) Provisional application No. 61/250,594, filed on Oct. 12, 2009.

(51) Int. Cl.
| | | |
|---|---|---|
| *A61K 31/44* | (2006.01) | |
| *A61K 31/47* | (2006.01) | |
| *A61K 31/473* | (2006.01) | |
| *A61K 48/00* | (2006.01) | |

(52) U.S. Cl.
CPC .............. *A61K 31/44* (2013.01); *A61K 31/47* (2013.01); *A61K 31/473* (2013.01); *A61K 48/005* (2013.01)

(58) Field of Classification Search
None
See application file for complete search history.

(56) References Cited

U.S. PATENT DOCUMENTS

| | | |
|---|---|---|
| 7,311,727 B2 | 12/2007 | Mazumder et al. |
| 2001/0036948 A1 | 11/2001 | Hearst et al. |
| 2005/0060028 A1 | 3/2005 | Horres et al. |
| 2005/0203069 A1 | 9/2005 | Arnold et al. |
| 2011/0183917 A1* | 7/2011 | Lu ................... C07K 14/43522 514/19.3 |
| 2012/0301458 A1* | 11/2012 | Rao ....................... A61K 31/519 424/133.1 |

FOREIGN PATENT DOCUMENTS

| | | | | |
|---|---|---|---|---|
| WO | WO-2006065827 A2 * | 6/2006 | ............... | C12N 7/00 |
| WO | 2008010984 A2 | 1/2008 | | |

OTHER PUBLICATIONS

Phillips et al., "P53 activation accelerates resolution of deep vein thrombosis," J Am Coll Surg (Sep. 2008).*
Steegenga et al., "Adenovirus E1A Proteins Inhibit Activation of Transcription by p53," Molecular and Cellular Biology, May 1996, pp. 2101-2109.*
Joffe et al., Upper-Extremity Deep Venous Thrombosis, Circulation 2002; 106:1874-1880.*
Sarkar et al., "Differential transcriptional activation of matrix metalloproteinaise-2 and membrane type-1 matrix metalloproteinase by experimentation deep venous thrombosis and thrombin," from the American Venous Forum, Journal of Vascular Surgery 2005.*
Deatrick et al., "Vein remodeling after deep vein thrombosis involves matrix metalloproteinases and late fibrosis in a mouse model," Journal of Vascular Surgery, vol. 42, No. 1, (2005).*
Office Action dated May 6, 2013 issued in related U.S. Appl. No. 13/501,278.
Carter, British Medical Journal, 1971, 1:312-314.
Office Action dated Nov. 7, 2013 issued in related U.S. Appl. No. 13/501,278.
Nguyen P.D., et al., Improved diabetic wound healing through topical silencing of p53 is associated with augmented vasculogenic mediators. Wound repair and regeneration: official publication of the Wound Healing Society [and] the European Tissue Repair Society. 2010;18:553-559.
Sood, V., et al., Vein wall remodeling after deep vein thrombosis: Differential effects of low molecular weight heparin and doxycycline. Ann Vasc Surg. 2009;24:233-241.
Kakkar, V.V., Prevention and management of venous thrombosis, British Medical Bulletin, 1994, vol. 50—No. 4 pp. 871-903.
Snook, G.A., et al., Thromboembolism after Surgical Treatment of Hip Fractures, Clinical Orthopaedics and Related Research, Mar.-Apr. 1981, No. 155, pp. 21-24.
Johansson, E., et al., Clinical and Experimental Evaluation of the Thromboprophylactic Effect of Hydroxychloroquine Sulfate after Total Hip Replacement, Haemostasis, 1981, vol. 10:89-96.
Office Action dated Aug. 28, 2014 issued in related U.S. Appl. No. 13/501,278.
Mickley, V., Stenois and Thrombosis in Haemodialysis Fistulae and Grafts: the Surgeon's Point of View, Nephrol Dial Transplant (2004) 19:309-311.
Office Action dated Sep. 28, 2015 issued in related U.S. Appl. No. 13/501,278.
Lynch, TJ, Jr., Management of malignant pleural effusions, Chest, Apr. 1993; 103(4 suppl):385S-389S (Abstract).
Porcel, J.M., et al., Pleural Effusions Due to Pulmonary Embolism, Curr Opin Med. 2008;14(4):337-342.
Sclerotherapy for varicose veins. Printed from http://www.surgeryencyclopedia.com/Pa-St/Sclerotherapy-for-Varicose-Veins.html.

(Continued)

*Primary Examiner* — Jared Barsky
(74) *Attorney, Agent, or Firm* — Miles & Stockbridge P.C.; David R. Schaffer

(57) ABSTRACT

A novel function for the p53 gene related to resolution of deep venous thrombosis is disclosed herein. Lack of the p53 gene results in impaired thrombus resolution in a clinically relevant in vivo model of deep venous thrombus resolution. It is further shown that augmentation of p53 activity with quinacrine accelerates thrombus resolution in vivo, and that this beneficial effect is completely dependent on p53. p53-based therapy is therefore provided to accelerate thrombus resolution in patients, and to prevent or ameliorate the debilitating long-term complications of deep venous thrombosis such as post-thrombotic syndrome.

12 Claims, 9 Drawing Sheets

(56) References Cited

OTHER PUBLICATIONS

Pleural Effusion—Heart & Vascular Institute Overview. Printed from https://my.clevelandclinic.org/health/diseases_conditions/pleural-effusion.
Office Action dated May 10, 2016 issued in related U.S. Appl. No. 13/501,278.
Dwyer, Surface-Treated Catheters—A Review, (published online Oct. 13, 2008).
Rand et al., Hydroxychloroquine directly reduces the binding of antiphospholipid antibody-β2-glycoprotein I complexes to phospholipid bilayers, Blood, Sep. 2008, vol. 112, No. 5.

* cited by examiner

ACCELERATING THROMBUS RESOLUTION THROUGH AUGMENTATION OF P53 ACTIVITY

STATEMENT AS TO RIGHTS TO INVENTIONS MADE UNDER FEDERALLY SPONSORED RESEARCH OR DEVELOPMENT

This invention was made with Government support under Grant No. HL083917, awarded by National Institutes of Health. The Government has certain rights in this invention.

FIELD OF THE INVENTION

The present invention relates to medical treatment. Specifically, the present invention relates to pharmacological and/or molecular treatment of thrombosis though augmentation of p53 activity to accelerate the resolution and healing of the thrombus.

BACKGROUND OF THE INVENTION

Blood clots in veins, also known as deep venous thrombosis, affects 1-2 million Americans per year. Deep venous thrombosis can lead to pulmonary embolism, in which the thrombus detaches and travels to the lungs where it can cause fatal cardiopulmonary complications. Pulmonary embolism from deep venous thrombosis is the leading preventable cause of in-hospital death and accounts for greater than 200,000 deaths per year in the U.S. The standard treatment for deep venous thrombosis is immediate anticoagulation which prevents the thrombus from propagating (growing) and subsequently detaching and inducing pulmonary embolism. Anticoagulation, if instituted promptly, is highly effective at preventing pulmonary embolism. Deep venous thrombosis has additional detrimental effects on the vein wall, however, and these changes can cause significant disability and disease. Delayed resolution (healing) of the thrombus results in vein wall and venous valve damage, and eventually can cause post-thrombotic syndrome in 25-75% of patients months to years after a deep venous thrombosis.

Post-thrombotic syndrome can include symptoms of swelling, pain and skin changes up to and including chronic non-healing ulcers of the skin. Post-thrombotic syndrome is due to increased venous pressure in the veins of the leg, and is caused by either loss of the venous valves due to scarring or persistent obstruction of the vein lumen by the thrombus. It is estimated that 2% of total health care costs in the United States are due to treatment of venous leg ulcers, and numerous studies have documented poor quality of life, persistent disability and repeated hospital admission in those patients suffering from venous leg ulcers, which are the most severe manifestation of post-thrombotic syndrome. Approximately 1% of individuals over the age of 65 have a venous leg ulcer per the General Practice Research Database.

These long-term complications of deep venous thrombosis have led to interest in pharmacologic and mechanical therapy to either remove the thrombus or accelerate the body's healing or resolution of the thrombus within the vessel wall. Treatment of deep venous thrombosis within two weeks of onset with thrombolytic therapy or mechanical thrombectomy is possible in some cases, and early clinical trials indicate that early removal of the thrombus results in improved long-term venous function in the leg. Thrombolytic therapy consists of specific enzymatic agents (e.g. tissue plasminogen activator) which cleave the fibrin within the thrombus. Several means of mechanical thrombus removal are also available, including balloon catheter devices (Fogarty catheter), high speed saline irrigation systems (Angiojet) and rotational wire/catheter devices (Trellis). These devices can be combined with pharmacologic thrombolysis as discussed above for greater potential efficacy.

The limitation of both pharmacologic and mechanical thrombectomy is that they are generally are ineffective in patients who present with thrombus of greater than 2 weeks duration. This is due to the natural change in the composition and structure of the thrombus itself over time, where the initial fibrin-rich mass is gradually replaced with a firmer, more fibrotic ingrowth of tissue. This fibrotic tissue is not responsive to the enzymatic action of pharmacologic thrombolysis and is also less amenable to mechanical thrombectomy methods. Thrombolytic therapy has a moderate risk of complications including bleeding from the puncture site, hematoma, rethrombosis and can also have rare but life-threatening complications (e.g. intracranial hemorrhage) which leads to caution in recommending their wide use to treat deep venous thrombosis. Thus, current treatment strategies aimed at deep venous thrombosis are limited to those patients who present for medical care within two weeks of the onset of the thrombosis, which is a subset of all patients with deep venous thrombosis. Both pharmacologic and mechanical thrombolysis are invasive procedures and carry the risk of serious complications.

Another strategy to decrease the detrimental effects of deep venous thrombosis on the vein wall and circulatory system is to accelerate the resolution of the thrombus by the body's own healing mechanisms. The resolution of deep venous thrombosis in patients has been studied with venography (which involves x-rays after injection of contrast material into the vein) as well as non-invasively with duplex ultrasound technology. These studies have demonstrated variable resolution of the obstructive thrombus over time in patients, which is noted as recanalization of the vein by either venography or ultrasound imaging. Those patients who demonstrate rapid resolution of the thrombus generally have improved clinical outcomes and less symptoms of post-thrombotic syndrome than patients with persistent venous obstruction noted by imaging studies.

A similar situation exists in the arterial circulation where thrombus results in the blockage of arteries and decreased flow of oxygenated blood to the downstream tissue. This is compensated for by collateral arteries which increase in size to allow circulation around the blockage. Some arterial thrombi are noted to recanalize over time, potentially allowing circulation through the previously blocked artery. As with deep venous thrombosis, arterial thrombosis can be treated with thrombolytic therapy if detected early, but no specific therapy exists to accelerate resolution of an arterial thrombus to increase the potential chances of recanalization of the artery and restoration of in-line blood flow.

The exact mechanisms of thrombus resolution are not well understood, as resolving deep venous thrombi are rarely if ever removed from patients to allow pathological examination. Thus, our knowledge of the biology and molecular mechanisms of thrombus resolution are largely derived from experimental animal models of deep venous thrombosis, in which pathological examination of the thrombus at different time points reveals a defined cascade of biological events that contribute to the resolution process.

In rodent models of thrombus resolution, the inferior vena cava is surgically ligated to generate a thrombus immediately below the ligature. This thrombus reaches a maximum size in 3-4 days and then undergoes a reduction in size and volume over time. Pathological examination of these thrombi over time demonstrate an early (1-2 days) infiltration of neutrophils into the initially fibrin- and red blood cell-rich thrombus, followed by a subsequent infiltration of macrophages (after 3-4 days) and ingrowth of capillary blood vessels and deposition of collagen. Studies utilizing such rodent models of thrombus resolution have shown an important role for certain genes in the thrombus resolution process, including urokinase-type plasminogen activator and heme oxygenase. Experimental studies designed to improve resolution of deep venous thrombosis with exogenous therapy have shown that gene transfer of the vascular endothelial growth factor (VEGF) gene using an adenovirus injected into the formed thrombus results in improvement in thrombus resolution as measured by thrombus weight at a subsequent time point (*Arteriosclerosis, Thrombosis, and Vascular Biology.* 2008; 28:1753.). It should be noted that injection of experimental thrombi with angiogenic peptide growth factors (VEGF protein rather than an adenovirus) targeted to accelerate thrombus resolution did not result in any improvement in the process of thrombus resolution. (J Vasc Surg. 2004 September; 40(3):536-42). Gene therapy with an adenovirus raises serious issues of toxicity and safety of viral vectors and is currently far from clinical use in patients. Treatment of animals with the cytokine macrophage chemotactic factor (MCP-1) does improve experimental thrombus resolution although this agent is not approved for use in humans (*J Vasc Surg.* 1999; 30: 894-899). Experimental animal studies using the widely available anticoagulant low molecular weight heparin have shown no improvement in the resolution of an established thrombus, which correlates with the clinical data demonstrating that prompt anticoagulation prevents pulmonary embolism but does not alter the resolution of the thrombus in the leg.

In summary, there is currently no specific pharmacologic therapy designed to accelerate resolution of such an established venous thrombosis. The majority of patients with deep venous thrombosis currently do not receive thrombolytic therapy or mechanical thrombectomy as they present after the two week window of time in which this type of therapy is effective at removing the thrombus. Thus, a large population of patients are at substantial risk of long-term development of post-thrombotic syndrome. Post-thrombotic syndrome is a debilitating condition that affects ambulation, the ability to work and overall quality of life. There is no effective treatment for post-thrombotic syndrome once it is established. A pharmacological means of accelerating the resolution of deep venous thrombosis has the potential to improve venous function by either decreasing the obstruction due to thrombus mass or preventing long-term scarring of the venous valves. There is therefore a definite need for pharmacologic or molecular means of accelerating the resolution of deep venous thrombi.

SUMMARY OF THE INVENTION

Disclosed herein is a novel function for the p53 gene, in the resolution of deep venous thrombosis. Furthermore the disclosure demonstrates that augmentation of p53 activity with a p53 activator such as quinacrine accelerates thrombus resolution in vivo. Disclosed herein is p53-based therapy to accelerate thrombus resolution in patients, and thereby prevent or ameliorate the debilitating long-term complications of deep venous thrombosis such as post-thrombotic syndrome.

Accordingly, a primary object of the present invention is to provide pharmacologic or molecular means of accelerating the resolution of deep venous thrombi.

Another object of the present invention is to define pharmacologic agents that accelerate resolution of a venous thrombosis and could be used systemically to treat a patient with a venous thrombosis to hasten its resolution and prevent secondary complications such as the post-thrombotic syndrome.

Another object of the present invention is to define pharmacologic agents that accelerate resolution of an established thrombosis and could be used either alone or in conjunction with other agents to treat a patient with an established arterial thrombosis to increase potential recanalization of the thrombosed artery and restoration of blood flow.

Another object of the present invention is to identify pharmacologic agents that could be administered via a catheter or other drug delivery device (e.g. a perforated or hydrogel balloon) remotely within the body to an area of either venous or arterial thrombosis to accelerate resolution of the thrombosis to restore normal blood flow and prevent secondary complications (e.g. post-thrombotic syndrome for deep venous thrombosis).

Another object of the present invention is to define pharmacologic agents that could be applied to an intravascular device such as a stent, vascular graft or other implantable vascular prosthesis for the purpose of accelerating resolution of thrombosis either present at the time of implantation or that develop subsequently to the implantation.

Another object of the present invention is to identify genes important in the process of thrombus resolution whose activity could be increased in or around sites of arterial or venous thrombosis by gene transfer of genetic material encoding these genes using plasmid DNA, viral vectors, biophysical adjuncts or some combination thereof. The purpose of this gene transfer would be to increase the expression of such genes to accelerate resolution of the thrombus.

The present invention discloses a novel role for the p53 gene in the process of deep venous thrombi resolution and demonstrates that augmentation of p53 function in a clinically relevant animal model of thrombus resolution results in accelerated thrombus resolution.

It is disclosed herein that the p53 gene is activated during the resolution of venous thrombosis and plays an important role in the process of thrombus resolution. It is further disclosed herein that that augmentation of p53 gene function can improve thrombus resolution.

There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter which illustrate preferred embodiments of the invention.

BRIEF DESCRIPTION OF THE DRAWINGS AND THE FIGURES

DETAILED DESCRIPTION OF THE INVENTION

In an effort to develop pharmacological and molecular therapy to accelerate thrombus resolution, the function of the p53 gene was studied in an in vivo model of thrombus resolution. In this mouse model (vena caval ligation) the thrombus shrinks between day 4 and day 12 by about 50% as defined by change in thrombus weight. It was noted that the expression of the p53 protein is increased in thrombus resolution.

p53, also known as protein 53 or tumor protein 53, is a tumor suppressor protein that in humans is encoded by the TP53 gene. To define the role of the p53 gene in the process of thrombus resolution, thrombus resolution in mice lacking the p53 gene was compared with normal (wildtype) mice. It was determined that mice genetically lacking p53 had impaired resolution of thrombus as defined by larger thrombi on day 12 in comparison with wildtype mice. This demonstrates that the p53 gene plays an important role in thrombus resolution. Specifically, in this model lack of the normal p53 gene impairs thrombus resolution.

In order to determine whether augmentation of normal p53 function could accelerate thombus resolution wildtype mice were treated with the p53 activator quinacrine (25 mg/kg body weight, by daily injection). Quinacrine is known to increase p53 levels by stabilizing the p53 protein and preventing its normal degradation inside cells. Animals treated with the p53 activator showed improved thrombus resolution as compared with animals that were injected with saline alone.

Figure 2:
FIG. 2 is a photograph of the mouse model of thrombus resolution taken on post-operative day 3 illustrating the surgical ligature at the upper aspect of the vena cava and the large thrombus notable within the vena cava.

To determine whether the beneficial effect on thrombus resolution of quinacrine was due to activation of the p53 gene and not some other unknown effect of quinacrine on thrombus resolution the quinacrine experiment was repeated in mice that lack p53 (FIG. 2). Here it was found that the benefit of quinacrine on thrombus resolution was absent in mice lacking p53, thereby demonstrating that the accelerated thrombus resolution with quinacrine was mediated by augmentation of p53 activity. This shows that increasing p53 function in vivo results in improved thrombus resolution, and is the first demonstration of augmentation of the p53 gene to achieve this goal.

It is therefore provided herein: a first demonstration of effective pharmacological therapy to accelerate resolution of an established venous thrombus; and experimental evidence that augmentation of p53 gene function accelerates thrombus resolution. Varying means of augmenting p53 function including but not limited to gene transfer of p53, and the application of pharmacologic agents that increase p53 protein and/or activity are known to one of ordinary skill in the art.

It is disclosed herein that administration of quinacrine in an in vivo model of thrombus resolution results in accelerated resolution, and that this beneficial effect is dependent on activation of the p53 gene. One skilled in the art of medicine and pharmacology could systemically administer quinacrine, or other activators of the p53 gene, including but not limited to chloroquine or other acridines, to accelerate resolution of thrombus in patients with arterial or venous thrombus. One skilled in the art of medicine and pharmacology could deliver activators of p53 via catheter or other local delivery device to areas of the circulation involved with thrombus to provide high local concentration of the agent to accelerate resolution of the thrombus. One skilled in the art of medicine and pharmacology could deliver gene therapy (using plasmid cDNA for p53, an adenovirus encoding p53 or a lentivirus encoding p53) to increase expression of the p53 protein in areas of thrombus by a catheter, infusion balloon or other localized delivery device. Contemplated delivery means further include for example a p53-encoding nucleic acid in a recombinant vector that expresses p53 protein. Such p53-expressing recombinant vector can include a naked DNA plasmid, a plasmid within a liposome, a viral vector or the like. The viral vector can be for example a retroviral vector or a recombinant adenoviral vector. The p53-encoding nucleic acid can be provided in an expression cassette. In one embodiment, the expression cassette can further include an SV40 early polyadenylation signal. The p53-encoding nucleic acid can be under the control of a constitutive promoter. In exemplary embodiments the constitutive promoter can be a cytomegalovirus promoter, RSV promoter, or SV40 promoter. For example, the constitutive promoter can be cytomegalovirus IE promoter. In an alternative embodiment at least one gene essential for adenovirus replication can be deleted from the recombinant adenoviral vector. For example, the E1A and E1B regions of the adenovirus vector can be deleted and the p53 expression cassette introduced in this region.

The well-established rodent model of thrombus resolution was used to define a role for the p53 gene in this process. In this model, a mouse is anesthetized, the abdomen is opened with standard sterile surgical technique and the vena cava (the largest abdominal vein) is ligated in the abdomen with a suture immediately below the level of the renal veins.

Figure 1:
FIG. 1 is a photograph taken during the execution of the mouse model of thrombus resolution.

FIG. 1 illustrates an intraoperative photograph of the vena cava where the suture is in position in the upper aspect of the image but has not yet been tied down. Ligation of the vena cava results in the predictable generation of a thrombus immediately below the ligature.

Figure 3:
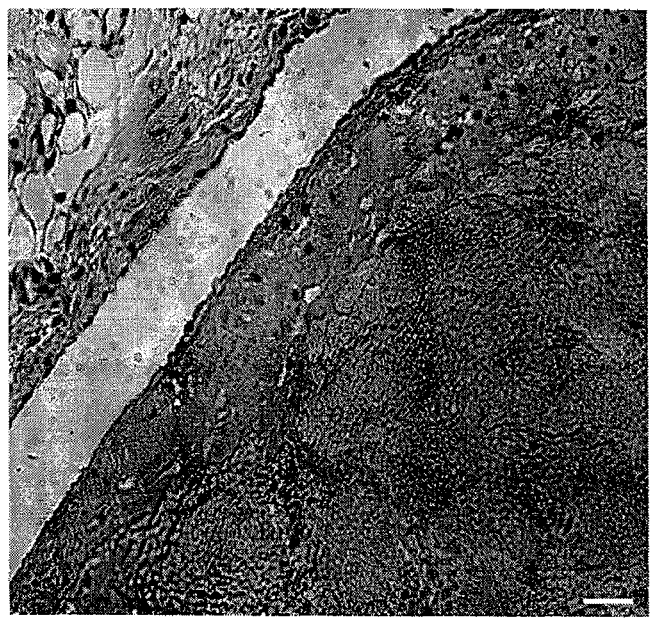
FIG. 3 is a photomicrograph of a thrombus from the mouse model harvested on post-operative day 3.
Figure 4:
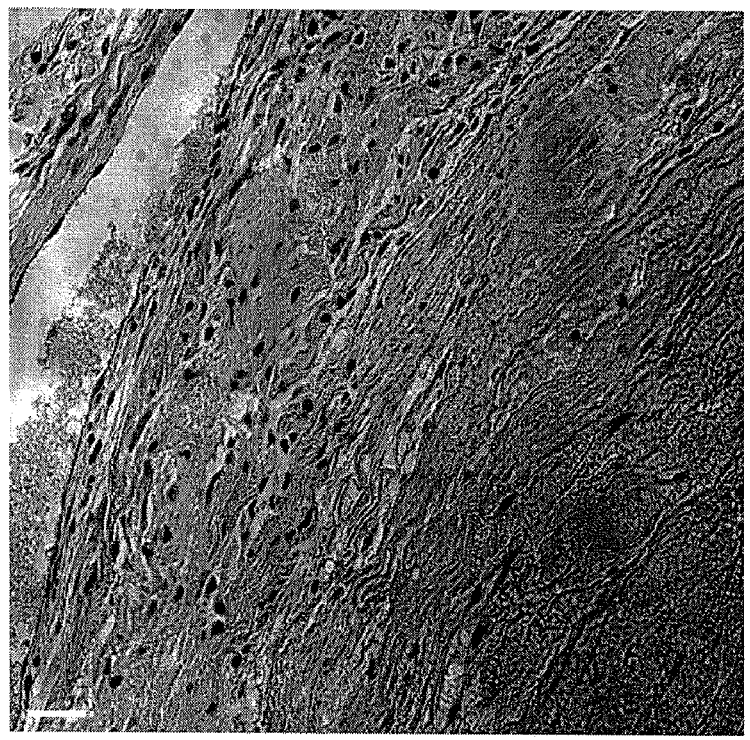
FIG. 4 is a photomicrograph of a thrombus from the mouse model harvested on post-operative day 12.

The thrombus increases in size for 3-4 days as shown in FIG. 2, which is an intraoperative photograph showing the thrombus within the vena cava 3 days after the ligature was placed. The thrombus then decreases in size for the next 14 days and this resolution corresponds with infiltration of the thrombus with inflammatory cells and collagen. This is shown in FIGS. 3 and 4, which are photomicrographs of thrombi harvested on day 3 and day 12, respectively, where the cellular composition of the thrombi has greatly increased on day 12 (FIG. 4) in comparison to day 3 (FIG. 3).

Figure 5:
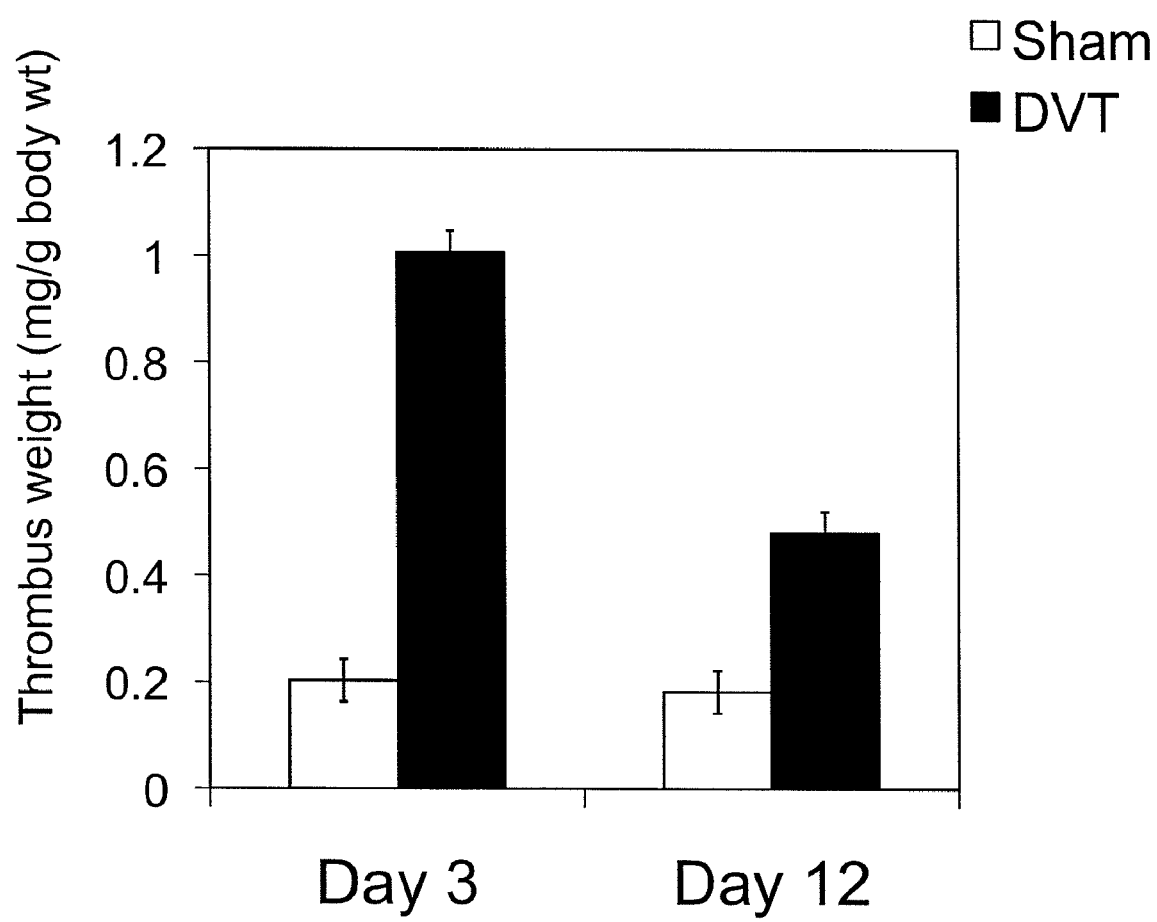
FIG. 5 is a graph illustrating the resolution of thrombus in the mouse model over time by comparing thrombus weights in animals at either post-operative day 4 or 12 after thrombus formation.

The weight of the thrombus decreases with time, and this change in weight reflects the thrombus resolution process in this model. This thrombus resolution is illustrated by FIG. 5, where the thrombus weight (normalized to the body weight of each animal at the time of sacrifice) is shown for thrombi harvested on day 3 and on day 12. The effects of abdominal surgery alone (without formation of a thrombus) on the weight of the vein are shown by the clear bars labeled "sham". There is approximately a 50% decrease in the mass of the thrombus between day 3 and day 12 (FIG. 5).

Figure 6:
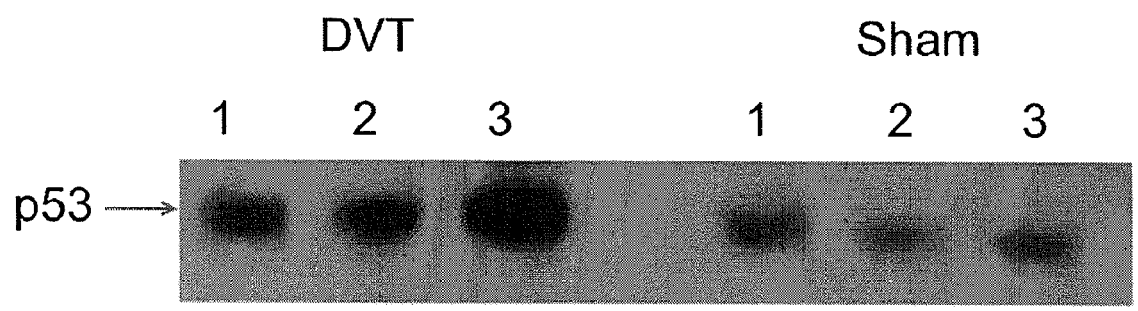
FIG. 6 is an immunoblot showing increased expression of p53 protein within the thrombus on post-operative day 12 in three animals that underwent thrombus formation (DVT, left) in comparison to three animals that underwent sham surgery (right).

The expression of the p53 gene during the process of thrombus resolution is illustrated by FIG. 6. As shown in FIG. 6, protein immunoblotting using gel electrophoresis shows that protein extracted from three thrombi at day 12 (labeled DVT, left lanes) show more p53 protein than three vena cava harvested 12 days after sham surgery (labeled sham, right lanes). Sham surgery animals were used as controls to ensure that any change in p53 protein levels would reflect the thrombus resolution and not residual inflammation from the surgical procedure itself. For this experiment, proteins were extracted from the thrombi or vena cava, processed for western blotting using standard acrylamide gel electrophoresis, transferred to nylon membranes and specifically probed with a commercially available antibody specific for the p53 protein.

Figure 7:
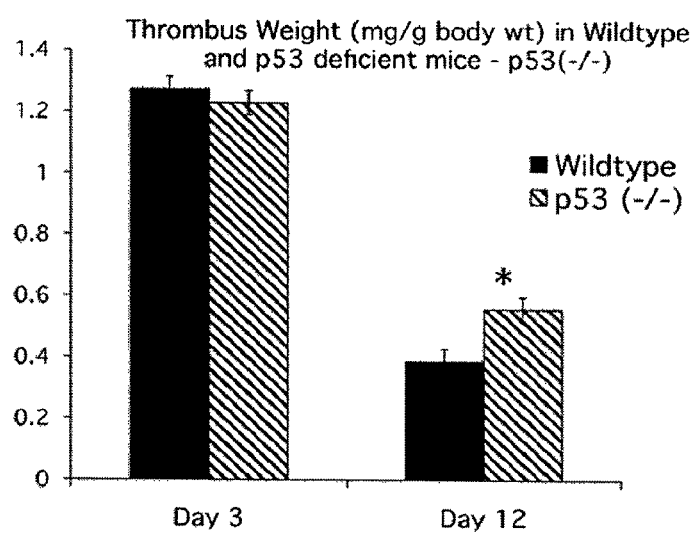
FIG. 7 shows the impaired thrombus resolution in mice lacking the p53 gene in comparison to normal (wildtype) mice as determined by thrombus weight on day 12.

To determine whether the activation of the p53 gene noted during thrombus resolution played any role in the process of thrombus resolution, thrombus resolution was studied in mice lacking the p53 gene. When thrombus resolution was studied in these commercially available mice (and normal mice for comparison), it was determined that mice lacking p53 had statistically larger thrombi on day 12, indicating that thrombus resolution was impaired in these mice (FIG. 7). This experiment was done with groups of 5-8 animals per time point and was statistically significant using student's t-test comparison. These studies demonstrated that the p53 gene plays a role during thrombus resolution. There was no significant difference between the normal mice and the mice lacking p53 in the size of the thrombi at day 3, indicating that the effect of p53 was specific to thrombus resolution and not the process of thrombus formation.

Figure 8:
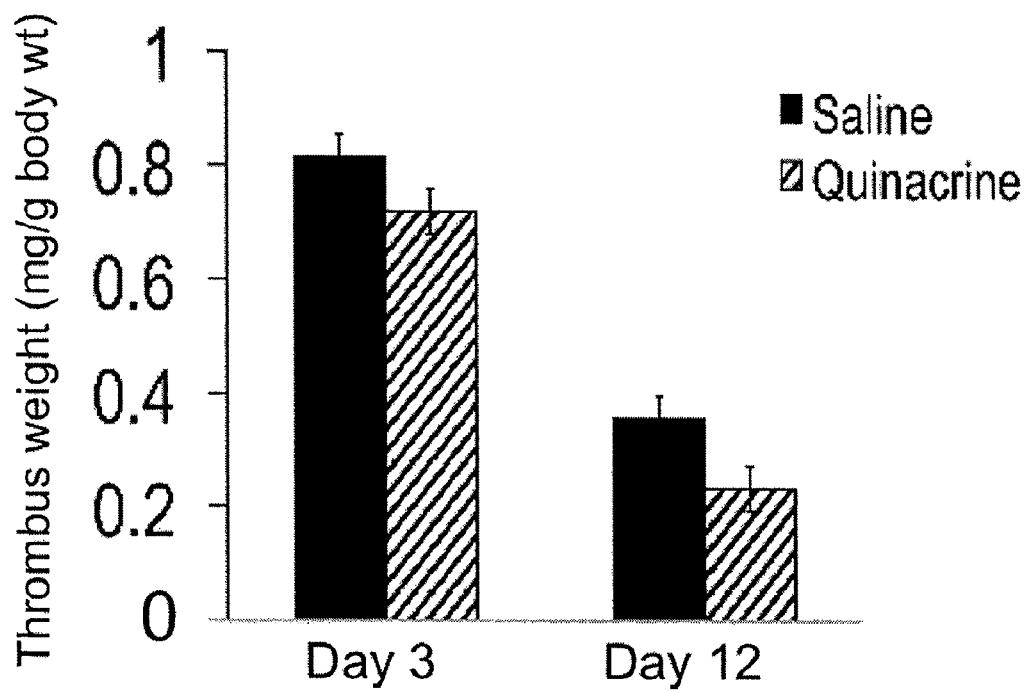
FIG. 8 shows the effect of administration of the p53 activator, quinacrine, on thrombus resolution as assessed by thrombus weight on day 12.

To determine if pharmacologic activation of the p53 gene beyond its usual activation by thrombus resolution might accelerate thrombus resolution, normal mice were treated with the p53 activator quinacrine (25 mg/kg body weight, by daily injection) or saline as a control, and then subjected to vena caval ligation as described above. It was found that quinacrine treatment accelerated thrombus resolution as determined by decreased thrombus weight on day 12 (FIG. 8). To determine if this effect of quinacrine was actually due to p53 activation, this experiment was repeated in animals lacking the p53 gene. The purpose of this experiment was to ensure that the demonstrated effects of quinacrine on thrombus resolution were due to activation of the p53 gene and not some other effect of the drug in the animal (so called "off-target effect").

Figure 9:
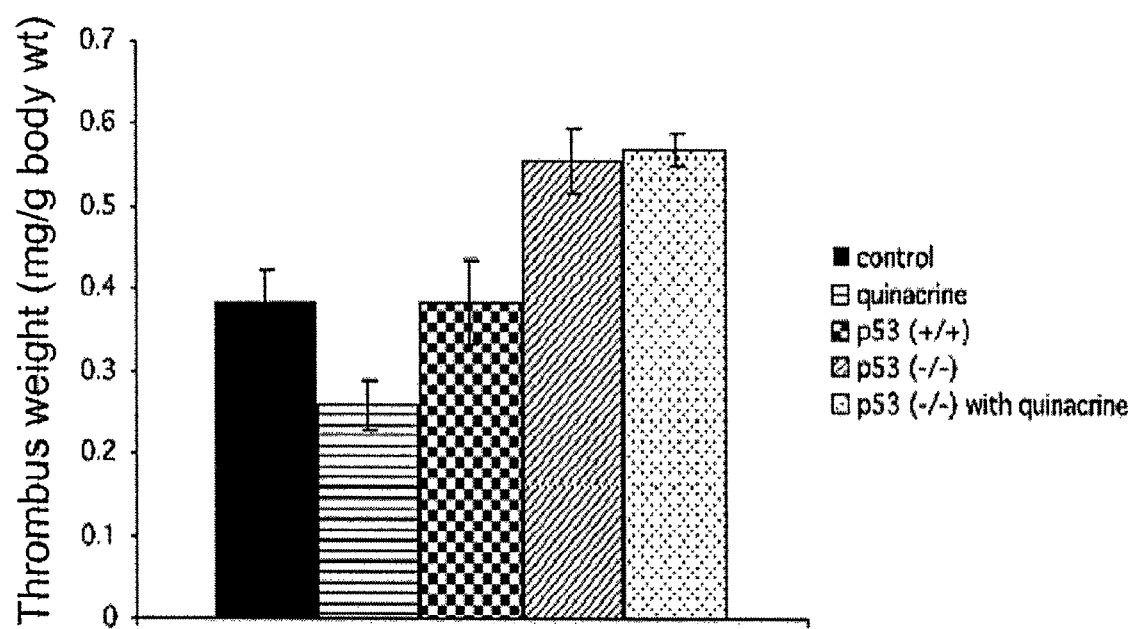
FIG. 9 shows the effect of quinacrine on thrombus resolution in normal mice (labeled control and quinacrine) and in mice lacking the p53 gene which are labeled p53(−/−).

When quinacrine was administered to mice lacking the p53 gene (labeled as p53(−/−) in the graph), there was no difference in thrombus size at day 12 (FIG. 9, last two columns), demonstrating that the beneficial effect of quinacrine on thrombus formation is dependent on the presence of, and thus mediated by, the p53 gene. Together these experiments demonstrate: 1) activation of the p53 gene during the thrombus resolution process, 2) a role for the p53 gene in mediating the normal process of thrombus resolution, 3) activation of the p53 gene pharmacologically results in improved thrombus resolution.

This invention demonstrates that pharmacologic augmentation of p53 activity can be used to treat patients suffering from deep venous thrombosis with the potential to accelerate resolution of the thrombus and decrease secondary complications of the thrombus within the vein wall.

In one embodiment the aforementioned pharmacologic agents are applied to an intravascular device such as a stent, vascular graft or other implantable vascular prosthesis. The pharmacologic agent is covalently bonded or otherwise chemically or physically attached to a stent, stent-graft, prosthetic graft, vena caval filter, artificial venous or arterial or cardiac valve, or other implantable vascular device for the purpose of accelerating the resolution of thrombus either present at the time of implantation or thrombus expected to develop post-implantation. Delivery systems are known by one of ordinary skill in the art and include but are not limited to controlled-release gel, biochemical coating, a p53 activator drug or gene delivery system (such as a plasmid encoding p53 gene), and the like.

Chemical modifications to known p53 activators (such as quinacrine) to prolong its pharmokinetic profile (such as half-life within the patient) or to increase its p53 activating ability are contemplated herein. One skilled in the art would test these modified compounds in the standard models of thrombus resolution (as shown in FIGS. 1-5) and could apply these to patients with either arterial or venous thrombosis for improved therapeutic efficacy or ease of drug closing for the purpose of accelerating thrombus resolution.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of accelerating the resolution of an established arterial or venous thrombus in a subject and increasing recanalization of a thrombosed artery or vein containing the established arterial or venous thrombus, the method comprising delivering to said subject therapeutically effective amounts of a p53-encoding nucleic acid to resolve the established arterial or venous thrombus, wherein the activator of the p53 gene was not administered to said subject prior to the arterial or venous thrombosis being established.

2. The method of claim 1, wherein the p53-encoding nucleic acid is in a recombinant vector that expresses p53 protein.

3. The method of claim 2, wherein the p53-expressing recombinant vector is a naked DNA plasmid, a plasmid within a liposome, or a viral vector.

4. The method of claim 3, wherein the viral vector is a retroviral vector or a recombinant adenoviral vector.

5. The method of claim 3, wherein the p53-expressing recombinant vector is a recombinant adenoviral vector.

6. The method of claim 2, wherein the p53-encoding nucleic acid is in an expression cassette.

7. The method of claim 6, wherein the expression cassette comprises the p53-encoding nucleic acid under the control of a constitutive promoter.

8. The method of claim 7, wherein the constitutive promoter is a cytomegalovirus promoter, RSV promoter, or SV40 promoter.

9. The method of claim 8, wherein the constitutive promoter is the cytomegalovirus IE promoter.

10. The method of claim 6, wherein the expression cassette further comprises an SV40 early polyadenylation signal.

11. The method of claim 5, wherein at least one gene essential for adenovirus replication is deleted from the recombinant adenoviral vector.

12. The method of claim 11, wherein the E1A and E1B regions of the adenovirus vector are deleted and the p53 expression cassette is introduced in their place.

* * * * *